United States Patent
Li et al.

(10) Patent No.: US 8,457,716 B2
(45) Date of Patent: *Jun. 4, 2013

(54) TIME OF FLIGHT BASED TRACHEAL TUBE PLACEMENT SYSTEM AND METHOD

(75) Inventors: Youzhi Li, Longmont, CO (US); Edward McKenna, Boulder, CO (US); Andy Lin, Boulder, CO (US); Sarah Hayman, Boulder, CA (US)

(73) Assignee: Covidien LP, Mansfield, MA (US)

( * ) Notice: Subject to any disclaimer, the term of this patent is extended or adjusted under 35 U.S.C. 154(b) by 289 days.

This patent is subject to a terminal disclaimer.

(21) Appl. No.: 12/434,770

(22) Filed: May 4, 2009

(65) Prior Publication Data
US 2010/0280362 A1    Nov. 4, 2010

(51) Int. Cl.
*A61B 5/00*   (2006.01)
*A61M 16/04*  (2006.01)

(52) U.S. Cl.
USPC ............. 600/424; 128/200.26; 128/207.14

(58) Field of Classification Search
USPC ............ 600/424; 128/200.26, 207.14, 207.15
See application file for complete search history.

(56) References Cited

U.S. PATENT DOCUMENTS

| | | |
|---|---|---|
| 4,344,436 A | 8/1982 | Kubota |
| 4,416,289 A | 11/1983 | Bresler |
| 4,431,005 A | 2/1984 | McCormick |
| 4,445,501 A | 5/1984 | Bresler |
| 4,567,882 A | 2/1986 | Heller |
| 4,943,770 A | 7/1990 | Ashley-Rollman et al. |
| 5,099,845 A | 3/1992 | Besz et al. |
| 5,291,262 A * | 3/1994 | Dunne .................. 356/5.06 |
| 5,400,771 A | 3/1995 | Pirak et al. |
| 5,425,370 A | 6/1995 | Vilkomerson |
| 5,425,382 A | 6/1995 | Golden et al. |
| 5,445,144 A | 8/1995 | Wodicka et al. |
| 5,560,351 A | 10/1996 | Gravenstein et al. |
| 5,622,169 A | 4/1997 | Golden et al. |
| 5,645,065 A | 7/1997 | Shapiro et al. |
| 5,785,051 A | 7/1998 | Lipscher et al. |
| 5,879,297 A | 3/1999 | Haynor et al. |
| 5,902,238 A | 5/1999 | Golden et al. |
| 6,129,668 A | 10/2000 | Haynor et al. |
| 6,132,379 A | 10/2000 | Patacsil et al. |
| 6,161,537 A | 12/2000 | Gravenstein et al. |

(Continued)

FOREIGN PATENT DOCUMENTS

| | | |
|---|---|---|
| WO | 03015610 | 2/2003 |
| WO | 2004030527 | 4/2004 |
| WO | 2008115928 | 9/2008 |
| WO | 2009099766 | 8/2009 |

OTHER PUBLICATIONS

Roberts, James R. et al., Proper Depth of Placement of Oral Endotracheal Tubes in Adults Prior to Radiographic Confirmation, Academic Emergency Medicine, Jan. 1995, pp. 20-24, vol. 2, No. 1.

(Continued)

*Primary Examiner* — Ruth S Smith

(57) ABSTRACT

According to various embodiments, a tracheal tube may employ optical sensing techniques for determining a distance between the inserted tube and an anatomical structure, such as a carina. The distance information may provide an indication as to whether or not the tracheal tube is properly placed within the trachea. The optical techniques may include time of flight techniques.

16 Claims, 4 Drawing Sheets

U.S. PATENT DOCUMENTS

| | | | |
|---|---|---|---|
| 6,164,277 | A | 12/2000 | Merideth |
| 6,216,028 | B1 | 4/2001 | Haynor et al. |
| 6,253,770 | B1 | 7/2001 | Acker et al. |
| 6,263,230 | B1 | 7/2001 | Haynor et al. |
| 6,332,089 | B1 | 12/2001 | Acker et al. |
| 6,349,720 | B1 | 2/2002 | Clark |
| 6,453,190 | B1 | 9/2002 | Acker et al. |
| 6,672,308 | B1 | 1/2004 | Gaspari |
| 6,705,319 | B1 | 3/2004 | Wodicka et al. |
| 6,860,264 | B2 | 3/2005 | Christopher |
| 7,717,312 | B2 * | 5/2010 | Beetel .................. 227/175.1 |
| 2002/0074002 | A1 | 6/2002 | Tung et al. |
| 2002/0139920 | A1 | 10/2002 | Seibel et al. |
| 2003/0034035 | A1 * | 2/2003 | Raphael ............... 128/207.14 |
| 2004/0039252 | A1 | 2/2004 | Koch |
| 2004/0221853 | A1 | 11/2004 | Miller |
| 2005/0038419 | A9 * | 2/2005 | Arnold et al. .............. 606/15 |
| 2006/0036164 | A1 | 2/2006 | Wilson et al. |
| 2006/0081255 | A1 | 4/2006 | Miller et al. |
| 2007/0137652 | A1 | 6/2007 | Qureshi et al. |
| 2008/0039715 | A1 | 2/2008 | Wilson et al. |
| 2008/0246943 | A1 * | 10/2008 | Kaufman et al. ........... 356/5.01 |
| 2009/0028407 | A1 * | 1/2009 | Seibel et al. ............... 382/131 |
| 2010/0179417 | A1 * | 7/2010 | Russo ........................ 600/424 |

OTHER PUBLICATIONS

Pollard, Richard J. MD et al., Endotracheal Tube Location Verified Reliably by Cuff Palpation, Anesthesia and Analgesia, 1995, pp. 135-138.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Locker, Gottfried J. MD et al., Assessment of the Proper Depth of Endotracheal Tube Placement with the Trachlight, Journal of Clinical Anesthesia, Aug. 1998, pp. 389-393, vol. 10.

Gaspari, Romolo J. MD et al., Magnetically Guided Orotracheal Intubation, Academic Emergency Medicine, Mar. 2001, pp. 285-287, vol. 8, No. 3.

Salem, M. Ramez MD, Verification of Endotracheal Tube Position, Anesthesiology Clinics of North America, Dec. 2001, pp. 1-18, vol. 19, Issue 4.

Juan, Eduardo J. et al., Miniature Acoustic Guidance System for Endotracheal Tubes, IEEE Transactions on Biomedical Engineering, Jun. 2002, pp. 584-596, vol. 49, No. 6.

Kristensen, Michael S. MD, The Parker Flex-Tip Tube Versus a Standard Tube for Fiberoptic Orotracheal Intubation, Anesthesiology, Feb. 2003, pp. 354-358, vol. 98, No. 2.

Kohase, Hikaru DDS, PhD et al., Endotracheal Intubation Device with a Charge Couple Device Camera, Anesthesiology, Dec. 2003, pp. 432-434, Issue 96.

Makino, Hiroshi MD et al., The Effects of Tracheal Tube Tip Design and Tube Thickness on Laryngeal Pass Ability During Oral Tube Exchanger with an Introducer, Anesthesia and Analgesia, Dec. 2003, pp. 285-288, Issue 97.

Chun, Rosaleen, MDm FRCPC et al., Where's the Tube? Evaluation of Hand-held Ultrasound in Confirming Endotracheal Tube Placement, Prehospital and Disaster Medicine, Nov. 2004, pp. 366-369, vol. 19, No. 4.

Monitoring of Intubation and Ventilation During Resuscitation, http://clinicaltrials.gov/ct2/show/NCT00204217, ClinicalTrials.gov, Aug. 2010, pp. 1-3.

O'Connor, Christopher J. MD et al., Identification of Endotracheal Tube Malpositions Using Computerized Analysis of Breath Sounds via Electronic Stethoscopes, Anesthesia and Analgesia, Dec. 2005, pp. 735-739, Issue 101.

Sehata, H et al., Tracheal Intubation using a new CCD Camera-Equipped Device: A Report of Two Cases with a Difficult Intubation, Acta Anaesthesiologica Scandinavica, Dec. 2005, pp. 1218-1220, Issue 49.

Weaver, Blake et al., Confirmation of Endotracheal Tube Placement after Intubation Using the Ultrasound Sliding Lung Sign, Academic Emergency Medicine, Mar. 2006, pp. 239-244, Issue 13.

Kaplan, M. B. et al., Seeing is Believing: the Importance of Video Laryngoscopy in Teaching and in Managing the Difficult Airway, Surgical Endoscopy and Other Interventional Techniques, Mar. 2006, pp. S479-S483, Issue 20.

Fridman, Ofer, Visual Sensor Provides a Breath of Fresh Air for Medical Ventilation, Medical Design Technology, Jul. 2006, pp. 11-13.

Wichakook, Want et al., Magnetic Endotracheal Tube Imaging Device, 30th Annual International IEEE EMBS Conference, Vancouver, Canada, Aug. 20-24, 2008, pp. 985-988.

Karsli, Cengiz, Head Movement Effect on Different Tracheal Tubes, http://clinicaltrials.gov/ct2/show/NCT00687583, ClinicalTrials.gov, Aug. 2010, pp. 1-3.

Schwarz, Uwe MD, Validation of Supra-Sternal Tube-Tip Palpatation (SSTTP), http://clinicaltrials.gov/ct2/show/NCT00690508, ClinicalTrials.gov, Aug. 2010, pp. 1-4.

* cited by examiner

TIME OF FLIGHT BASED TRACHEAL TUBE PLACEMENT SYSTEM AND METHOD

BACKGROUND

The present disclosure relates generally to medical devices and, more particularly, to airway devices, such as tracheal tubes.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, a patient may be intubated when an endotracheal tube is inserted through the patient's mouth and into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. During an intubation procedure, a practitioner may employ a lighted laryngoscope during introduction of the endotracheal tube. However, often the visualization of the trachea is poor because of patient secretions that may obscure the laryngoscope. In addition, such visualization during introduction of the tube may not account for ongoing changes in the tube's position within the trachea that may occur when a patient coughs, which may dislodge a tube from its desired location, or when a patient is jostled or moved within a care setting, which may change the position or angle of the tube within the trachea.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
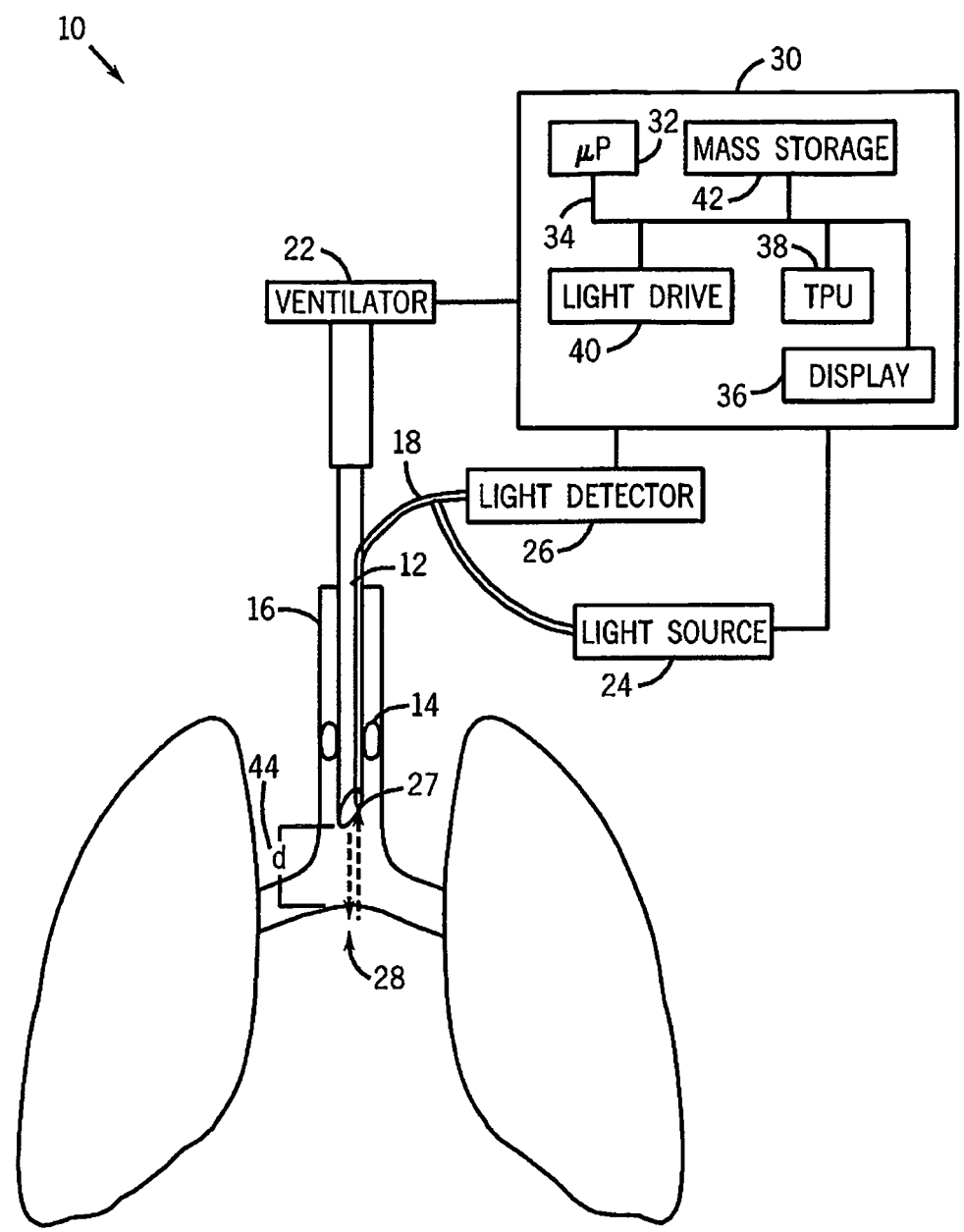
FIG. 1 illustrates an exemplary system including an endotracheal tube with a coherent light source and detector.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs when properly inserted into a patient's trachea. Positioning the tracheal tube at a desired position within the trachea, for example during endotracheal intubation, may improve the performance of the tracheal tube and reduce clinical complications. In particular, the distal inserted end of the endotracheal tube may be positioned in the patient's trachea at a location substantially between the patient's vocal cords and carina. If the tube cuff is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal tip of the tube may result in improved ventilation to the patient.

Provided herein are tracheal tubes and systems for facilitating proper placement of the tracheal tube relative to certain anatomical structures in and around the patient's airway and trachea. Such tracheal tubes may include assemblies for shining light into the trachea and detecting the returned light. The time of flight of the detected light may be affected by its interaction with an anatomical structure. Accordingly, information related to the time of flight of the detected light may be used to determine a distance from the tube to the anatomical structure in question. In certain embodiments, a distance from the distal end of the tracheal tube to the carina may be determined. A healthcare provider may then use the information about the location of the tracheal tube relative to the carina to determine whether the tube is properly placed or whether the position of the tube should be adjusted.

In certain embodiments, the disclosed tracheal tubes, systems, and methods may be used in conjunction with any appropriate medical device, including, without limitation, a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

FIG. 1 shows an exemplary tracheal tube system 10 that has been inserted into a patient's trachea. The system 10 includes a tracheal tube 12, shown here as endotracheal tube, with an inflatable balloon cuff 14 that may be inflated to form a seal against tracheal walls 16. The tracheal tube 12 may also include one or more optical conductors, e.g., optical fibers 18 that are associated with the tube 12. The optical source fiber 18 may be configured to pass light from a source 24 through a distal end 27 of the endotracheal tube and into a patient's trachea such that a portion of the emitted light may interact with a carina 28. The emitted light may be transferred back through the optical fiber 18 (or a different fiber or fibers), which may be coupled to a light detector 26.

The system 10 may also include devices that facilitate positive pressure ventilation of a patient, such as a ventilator 22, which may include any ventilator, such as those available from Nellcor Puritan Bennett LLC. The system may also include a monitor 30 that may be configured to implement embodiments of the present disclosure. The monitor 30 may be a stand-alone device or may be coupled to another patient monitor or to the ventilator 22. The monitor 30 may include a microprocessor 32 coupled to an internal bus 34 and a display 36.

The monitor 30 may include certain elements for controlling the light source 24 and the light detector 26. The monitor 30 may drive light from source 24, which in turn may be carried by optical fiber 18. The light may pass into the tissue, where it may be variously scattered, absorbed, and/or reflected and then detected by detector 26. A time processing unit (TPU) 38 may provide timing control signals to light drive circuitry 40, which controls when the light source 24 is activated, and if multiple light sources 24 are used, the multiplexed timing for the different light sources. TPU 38 may also control the gating-in of signals from detector 26.

In an embodiment, the monitor 30 may be configured to receive signals from the detector 26 and store the signals in a mass storage device 42, such as a RAM, ROM, optical storage device, flash memory device, hardware storage device, magnetic storage device, or any other suitable device permitting memory storage. The signals may be accessed and operated according to instructions for a microprocessor 32. In certain embodiments, the signals may be related to a placement of the tracheal tube 12 within the patient's trachea and may be processed by the monitor 30 to indicate whether the tracheal tube 12 is properly placed. The monitor 30 may be configured to provide an indication about the placement of the tracheal tube 12 within the patient's trachea, such as an audio alarm, visual alarm or a display message if the tracheal tube 12 is too far or too close to certain anatomical structures, such as the carina 28, or outside of a predetermined placement range. In an exemplary embodiment, based at least in part upon the received signals corresponding to the light received through optical fiber 18, microprocessor 32 may calculate a placement parameter of the endotracheal tube 12 using various algorithms. For example, the placement parameter may relate to a distance 44, or d, between the distal end 27 of the tube 12 and the carina 28 or other anatomical structure.

Figure 2:
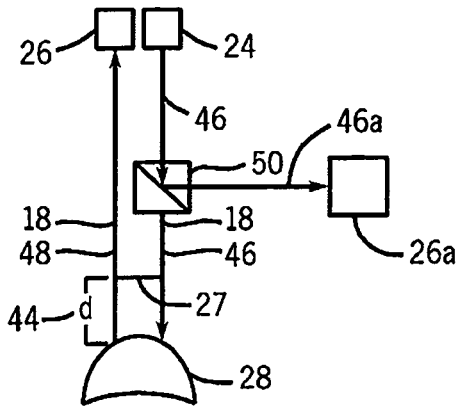
FIG. 2 is a schematic diagram of optical sensing components that may be coupled to a tracheal tube.

FIG. 2 is a schematic representation of an optical sensor arrangement that may be incorporated into system 10 for analyzing placement of a tracheal tube 12 within a patient's trachea. A light beam 46 from source 24 may be emitted from the distal end 27 of tube 12. The light may pass through the airway until the light interacts with an anatomical tissue structure, such as a carina 28. The light may travel a distance 44 before at least a portion of the light is returned. As noted, light from source 24 may be transmitted through optical source fiber 18 and the returned light beam 48 may pass through the same fiber 18 or may pass through a separate, dedicated return light beam fiber. The returned light beam 48 may be detected by light detector 26 to generate light signals that may be analyzed by monitor 30.

It should be understood that the depicted embodiments are exemplary, and the relationships between the optical components may vary. In particular, in embodiments in which optical fibers 18 are employed, the spatial relationships between light source 24, detector(s) 26, and beam splitter 50 (or optical coupler or multi-port circulator) may be altered. FIG. 2 depicts an embodiment in which the optical fiber 18 transmits light 46 and collects the returned light 48. As shown, the emitted light 46 is split at beam splitter 50 so that a portion of the light, light beam 46a, is directed towards a detector 26a, which may then generate a reference signal related to the time of flight of the emitted light 46. For example, because the distance of the emitter 24 to the detector 26a may be known, the reference beam may serve as a calibration for associating a known distance with a measured time of flight. The light beam 46 may pass through the airway until the light interacts with an anatomical tissue structure, such as a carina 28. The returned light beam 48 may be collected be returned through the optical fiber 18 and detected by light detector 26 to generate time of flight signals that may be analyzed by monitor 30. In certain embodiments, it is contemplated that a reference beam 46a may not be used and the time of flight may be calculated directly from the time of flight of the round trip of emitted beam 46 and the returned beam 48. In such embodiments, a beam splitter 50 may not be incorporated into system 10.

By determining the time of the light from the emitter 24 to reach the detector, for example the time of flight relative to a reference, the distance 44 may be determined. The signal generated at one or more detectors 26 may be communicated to the downstream monitor 30. The incoming signals may include a light signal from the detector 26, which may be analyzed to provide a time of flight of the emitted light beam 46. The incoming signals may also include a signal from the returned light beam 48. In addition, the TPU 38 may provide time stamp or other data to accompany the signals. For example, a TPU 38 may generate a time stamp for a light pulse emitted by the light source 24 and may generate a time stamp for the time that the corresponding returned light beam 48 impinges the detector 26. The monitor 30 may control the light source 24 and light detector 26. The TPU 38 may control the gating of signals from the light detector 26 in conjunction with the light drive circuitry 40. In certain embodiments, the monitor 30 may control a switch from emitting light to detecting light within the optical fiber 18.

The light source 24 and a detector 26 may be of any suitable type. For example, the light source 24 may be one or more light emitting diodes adapted to transmit one or more wavelengths of light, for example in the red to infrared range, and the detector 26 may be one or more photodetectors (e.g., photodiodes) selected to receive light in the range or ranges emitted from the light source 24. A light source 24 may be a coherent light source, such as a laser diode or a vertical cavity surface emitting laser (VCSEL). In one embodiment, the light source 24 may be a high speed pulsed light source and the detector 26 may be a high speed detector. In certain embodiments, the detector may be a time of flight camera. The light source 24 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics, such as optical fiber 18. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

In embodiments, the light source 24 and detector 26 may be directly coupled to the distal end 27 of the tracheal tube 12, such that the light does not first pass through an optical fiber 18 before being emitted or detected. In such an embodiment, any distance between the light source 24 and detector 26 may be accounted for in calculating the time of flight of the returned light.

Figure 3:
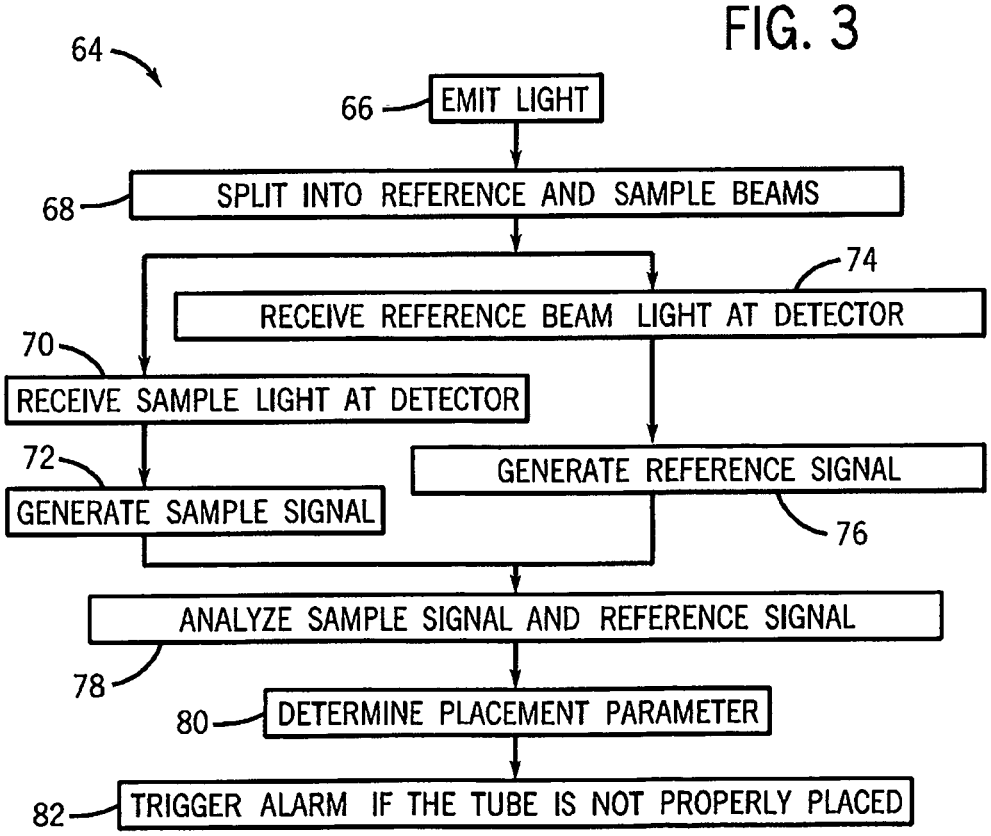
FIG. 3 is a flow diagram of a method of operating a tracheal tube.

FIG. 3 is a process flow diagram illustrating a method of determining placement of an endotracheal tube 12 in accordance with some embodiments. The method is generally indicated by reference number 64 and includes various steps or actions represented by blocks. It should be noted that the method 64 may be performed as an automated procedure by a system, such as system 10. Further, certain steps or portions of the method may be performed by separate devices. For example, a first portion of the method 64 may be performed by a light source 24 and light detector 26, while a second portion of the method 64 may be performed by a monitor 30. In embodiments, the method 64 may be performed continuously or intermittently for long-term patient monitoring or at any appropriate interval depending on the particular situation of the intubated patient. Further, the steps of method 64 may be performed during insertion of the tracheal tube 12 into the patient.

According to the exemplary embodiment illustrated, the method 64 begins with emitting light, at step 66 from a light source 24, which may be coupled to one or more optical fibers 18. The emitted light beam 46 is transmitted through fiber 18, which is associated with tube 12 that is inserted into a patient's airway. The portion of the emitted light is split at step 68 into a reference light beam 46a. The rest of the beam 46 may exit the distal end 27 of the tube 12 before interacting with anatomical structures in the patient. The returned light beam 48 that is returned through optical fiber 18 and received by the detector 26 at step 70 may provide information about the relative position of the tube 12 and the anatomical structure that is carried in the sample signal, generated at step 72. The delay between the time of the beam 46 exiting the emitter 24 and impinging detector 26, may be used to calculate a placement parameter. At step 74, a reference beam is detected by the detector 26 to generate a reference signal that is associated with a known distance at step 76.

A monitor 30 may perform analysis of the sample signal and the reference signal at step 78. In certain embodiments, the monitor may amplify and/or filter one or both of the sample signal and the reference signal prior to the analysis. A monitor 30 may determine a placement parameter at step 80 to determine if this distance 44, d, between the distal end 27 and the carina 28 associated with a desirable placement of the tracheal tube 12. In one embodiment, the analysis may include determining the distance 44 between the distal end 27 to the carina 28 by determining the distance associated with a measured time of flight delay, which in embodiments may be determined by the following equation:

$$TOF_{delay} = 2 \times (d/3 \times 10^8 \text{ m/s})$$

This $TOF_{delay}$ may thus represent twice the distance from the emitter 24 to the carina 28. The distance from the distal tip 27 to the carina 28 may then be determined by subtracting known parameters, such as the distance from the emitter 24 to the end of the fiber 18 at the distal tip 27. The distance of the reference beam 46a may be set to this distance (or, in certain embodiments, two times the distance to account for the return trip) to provide a reference for the delay associated with light traveling from the emitter 24 down the length of the tube 12. However, as noted, the distance d may be calculated directly from the $TOF_{delay}$ without the use of a reference if the distance from the emitter 24 to the distal tip 27 is known. The calculated distance d may then be used to determine a placement parameter at step 80. In one embodiment, a placement parameter may be a ratio of a calculated distance and an empirically derived or clinically measured distance associated with proper tube placement. It should be appreciated that there may be several empirically derived distances, depending on the size, age, or sex of the patient. A placement parameter may also be an average or mean of multiple data points or measurements. A placement parameter may also include a graphical, visual, or audio representation of the tube/anatomical structure distance. For example, a placement parameter associated with proper placement may include green light indicated on a display or a short tone generated by a speaker associated with monitor 30. Similarly, a placement parameter associated with improper placement of the tube 12 may trigger an alarm at step 82, which may include one or more of an audio or visual alarm indication. In one embodiment, the alarm may be triggered if the placement parameter is substantially greater than a predetermined value, substantially less than a predetermined value, or outside of a predetermined range. For example, proper tube placement may involve comparing a measured distance d of the distal end 27 to carina 28 to a predetermined range of 1-5 cm. In an embodiment, the predetermined target distance may differ for adult men, who may have, in an embodiment, a target distance of 3-4 cm, and adult women, for whom the target distance may be 2-3 cm. In other embodiments, the alarm may be triggered if the measured distance d is less than 3 cm, less than 2 cm, or less than 1 cm.

In one embodiment the time of flight measurements may employ a range determining output beam that is emitted from a high modulation bandwidth laser diode. A short laser pulse is emitted at a given frequency (e.g., on the order of tens of kHz). For each pulse, the time elapsed between emission and receipt of the returning pulse is measured. The measured time is proportional to the distance between the detector and the closest anatomical structure in the optical path of the emitted light.

Alternatively, a continuous laser emission scheme may be used, where timing of samples received corresponds to a specific time of emission of the laser light. Also, in some embodiments, light is emitted from a directly modulated laser diode using a high modulation bandwidth of optical intensity. Distance may be determined by sampling at a time period corresponding to the modulation to determine time elapsed between emission and receipt of corresponding returning light. The time elapsed is proportional to the distance to a closest point on the target surface.

In one embodiment, the method 64 may be performed by using an electronically tunable laser diode that may be frequency modulated continuously to determine short range sensing is used. A signal with a time-varying frequency modulates the range-finding output beam. The returning beam is mixed with a reference signal to produce a beat frequency which is a function of the distance to the target surface.

In a presently contemplated embodiment, the method 64 may be performed by using imaging LIDAR (light detection and ranging). Imaging LIDAR may employ arrays of high speed detectors as light detector 26 and modulation sensitive detector arrays typically built on single chips using CMOS and hybrid CMOS/CCD fabrication techniques. In these devices each pixel performs some local processing such as demodulation or gating at high speed, down-converting the signals to video rate so that the array may be read like a camera. Using this technique, many thousands of pixels/channels may be acquired simultaneously. Accordingly, LIDAR may provide additional data points for determining placement relative to anatomical structures.

Figure 4:
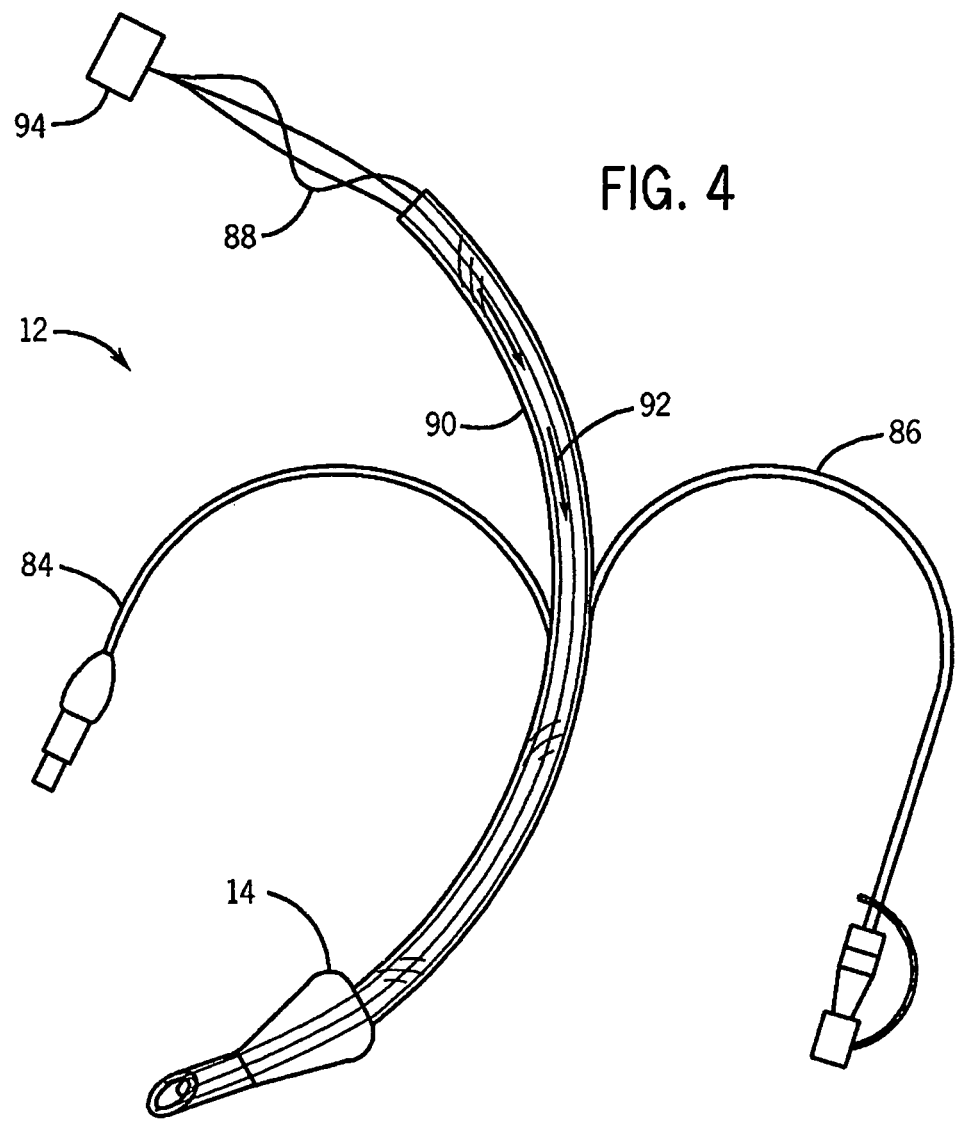
FIG. 4 is a perspective view of an exemplary endotracheal tube of FIG. 3.

FIG. 4 is a perspective view of an exemplary tracheal tube 12 according to certain embodiments. As shown, the tube 12 may include a cuff 14 that may be inflated via inflation lumen 84. The tracheal tube 12 may also include a suction lumen 86 for aspirating secretions that may form above the cuff 14. The tracheal tube 12 may also include a plurality of fibers or fiber bundles 88. Each fiber bundle may include one or more optical fibers 18. In certain embodiments, the transmitting and detecting may also take place within a single fiber. As shown, the fiber bundles 88 may extend through the walls 90 of the tracheal tube 12 such that they are substantially in line with a flow path 92 of the tracheal tube 12. The fibers bundles 88 may include any appropriate optical connector 94 for connecting the fiber bundles 88 to downstream components of the system 10, such as the beam splitter 46 or the light source 24 or light detector 26.

The tube 12 and the cuff 14 may be formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In embodiments, the cuff 14 may be generally sized and shaped like a typical high volume, low pressure cuff that may be designed to be inflated to pressures between about 15 cm $H_2O$ and 25 cm $H_2O$. The system 10 may also include a respiratory circuit (not shown) connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

Figure 5:
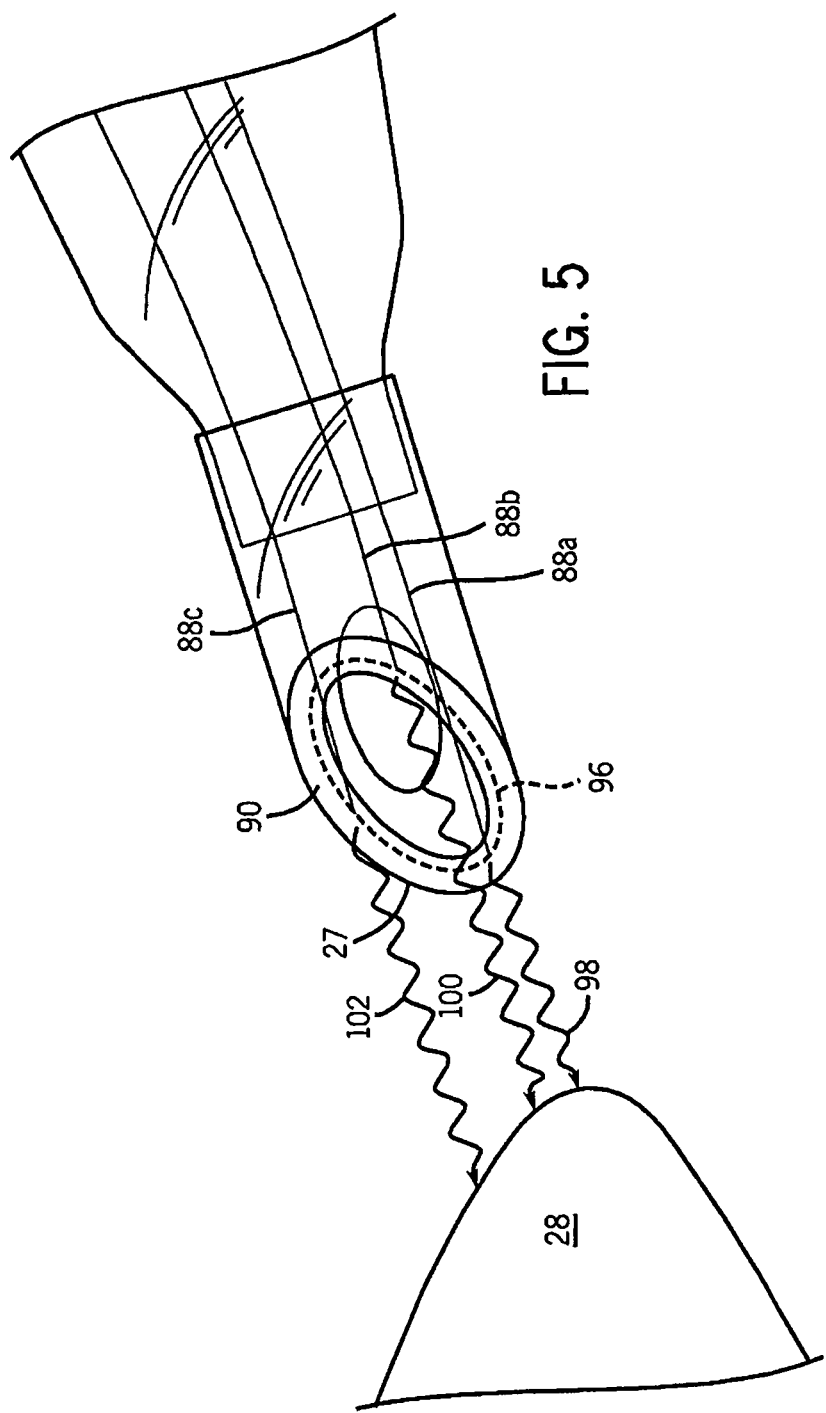
FIG. 5 is a perspective view of an exemplary distal tip of a tracheal tube with embedded optical fibers for a light source and detector.

FIG. 5 is a side view of the distal end 27 of the tracheal tube 12. As shown, the fiber bundles 88 may extend through the walls 90 of the tracheal tube. In embodiments, the fiber bundles 88 may be embedded or coextruded within an extruded tube tracheal tube 12. When the tube 12 is manufactured, the distal end 27 may be cut on a slant to facilitate insertion of the tube 12 in the trachea. After the tube is cut, the fiber bundles 88 may be terminated by any suitable technique.

The fiber bundles 88, or, in certain embodiments, individual fibers, may be distributed around the circumference 96 of the tube wall 90. In an embodiment, three optical bundles may be substantially evenly spaced about the circumference 96.

As shown the positioning of the fiber bundles 88 or single fibers may influence the path of the light from the distal end 27 of the tube 12 to the anatomical structure. Arrows 98, 100, and 102 illustrate three different light paths from bundles 88a, 88b, and 88c, respectively, to anatomical structures at or proximate to the carina 28. Arrow 98 has a somewhat shorter path than arrow 100, which is related to its position around the circumference 96 relative to the carina 28, as well as differences in the topography of the carina 28. In addition, slight changes in the angle within the trachea of the distal end 27 of the tube 12 may influence the path of light to and from the fiber bundles 88. In embodiments, light detected from all three fiber bundles 88 may be combined or averaged to generate the data used to determine a placement parameter. In addition, the differences in path length between multiple bundles may be used to determine a placement parameter that is indicative of the orientation of the distal end 27 within the trachea. Changes in this orientation (e.g., angular displacement) may indicate a shift in tube placement that may influence cuff pressure and sealing.

In certain embodiments, the fibers or fiber bundles 88 may be formed from materials such as quartz, glass, or a transparent plastic, such as poly(methyl methacrylate) or polystyrene with a fluoropolymer cladding. Examples of optical fibers include single-mode fibers, multi-mode fibers, photonic-crystal fibers, hollow-core fibers, polarization-maintaining fibers and dual-clad fibers. Typical diameters for optical fibers are from 5 to 1,000 micrometers. The optical fiber may be a single-mode fiber or a multi-mode fiber.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube placement relative to anatomical structures in the tracheal, but these techniques may also be utilized for the measurement and/or analysis of the placement of other suitable medical devices relative to other anatomical structures. For example, the present techniques may be utilized for the measurement and/or analysis of tracheal tubes relative to tracheal walls or the vocal cords. In addition, the present techniques may be employed in determining appropriate placement of any medical device, such as a stent, catheter, implant, feeding tube, cardiac device, drug delivery device, or pump. Rather, the various embodiments may cover all modifications, equivalents, and alternatives falling within the spirit and scope of the disclosure as defined by the following appended claims.

What is claimed is:

1. A method for determining placement of a tracheal tube in a subject comprising the steps of:
    emitting a light from a plurality of optical conductors circumferentially spaced about a beveled distal end of a tracheal tube disposed in a subject, wherein the beveled distal end is slanted relative to a wall of the tracheal tube;
    receiving the light returned from an anatomical structure within the subject;
    measuring a time of flight of the light from each of the plurality of optical conductors; and
    determining an orientation of the tracheal tube based upon the time of flight of the light from each of the plurality of optical conductors and a difference in path length between the plurality of optical conductors, wherein the difference in path length is representative of a position of each respective optical conductor about the beveled distal end.

2. The method of claim 1, comprising measuring a time of flight of a reference, and wherein the orientation is determined based upon the time of flight of the returned light from the plurality of optical conductors and the time of flight of the reference.

3. The method of claim 1, wherein the orientation is representative of a comparison of a distance between the plurality of optical conductors circumferentially spaced about the beveled distal end tracheal tube and the anatomical structure.

4. The method of claim 3, wherein the anatomical structure comprises a carina.

5. The method of claim 4, comprising triggering an alarm when a distance between the tracheal tube and the carina is less than a predetermined distance or when the distance between the tracheal tube and the carina falls outside of a predetermined range.

6. The method of claim 1, wherein the steps are performed during intubation of the subject.

7. The method of claim 1, wherein the steps are performed after intubation of the subject.

8. A system for determining placement of a tracheal tube in a subject comprising:
- a tracheal tube comprising a plurality of optical conductors circumferentially spaced apart on a beveled distal end of the tracheal tube, wherein the beveled distal end of the tracheal tube is angled relative to a wall of the tracheal tube;
- a light source configured to emit a light through each of the respective plurality of optical conductors when the tracheal tube is disposed in a subject;
- a photodetector configured to receive the light emitted from each of the respective plurality of optical conductors after interaction with an anatomical structure within the subject; and
- a processor configured to determine an orientation related to a placement of the tracheal tube in the subject based upon a time of flight of the light from each of the respective plurality of optical conductors and a difference in path length between the plurality of optical conductors, wherein the difference in path length is representative of a position of each respective optical conductor about the beveled distal end.

9. The system of claim 8, comprising a beam splitter configured to split a portion of the light into a reference beam.

10. The system of claim 9, comprising a second photodetector configured to receive the reference beam.

11. The system of claim 8, wherein the anatomical structure comprises a carina.

12. The system of claim 11, wherein the processor is configured to trigger an alarm when a distance between the tracheal tube and the carina is less than a predetermined distance or when the distance between the tracheal tube and the carina falls outside of a predetermined range.

13. The system of claim 8, wherein the light source comprises a laser diode configured to emit pulses of light.

14. The system of claim 8, wherein the light source comprises a tunable laser.

15. A device for determining placement of a tracheal tube in a subject comprising:
- a processor configured to:
- drive a light source configured to emit light through a plurality of optical conductors circumferentially spaced about a beveled distal end of a tracheal tube disposed in a subject;
- receive a signal from a photodetector configured to receive returned light from an anatomical structure within the subject; and
- determine an orientation of the tracheal tube in the subject based upon a time of flight of the returned light from each of the plurality of optical conductors and a difference in path length between the plurality of optical conductors, wherein the difference in path length is representative of a position of each respective optical conductor about the beveled distal end; and
- a display configured to provide an indication of the orientation.

16. The device of claim 15, wherein the processor is configured to trigger an alarm based on the orientation of the tracheal tube in the subject.

* * * * *